(12) United States Patent
Hays (10) Patent No.: US 11,260,437 B2
(45) Date of Patent: Mar. 1, 2022

(54) CLEANING AND SEPARATING MEDICAL WASTE

(71) Applicant: Brian Michael Hays, Little Elm, TX (US)

(72) Inventor: Brian Michael Hays, Little Elm, TX (US)

( * ) Notice: Subject to any disclaimer, the term of this patent is extended or adjusted under 35 U.S.C. 154(b) by 462 days.

(21) Appl. No.: 15/813,305

(22) Filed: Dec. 8, 2017

(65) Prior Publication Data

US 2018/0141094 A1  May 24, 2018

Related U.S. Application Data

(60) Provisional application No. 62/425,359, filed on Nov. 22, 2016.

(51) Int. Cl.
*B09B 3/00* (2022.01)
*B03C 1/23* (2006.01)
(Continued)

(52) U.S. Cl.
CPC ............ *B09B 3/0075* (2013.01); *A61L 11/00* (2013.01); *B02C 18/0084* (2013.01); *B02C 23/10* (2013.01); *B02C 23/14* (2013.01); *B02C 23/20* (2013.01); *B03B 9/061* (2013.01); *B03C 1/035* (2013.01); *B03C 1/23* (2013.01); *B03C 1/30* (2013.01); *B03C 7/00* (2013.01); *B29B 17/02* (2013.01); *C22B 1/005* (2013.01); *C22B 7/005* (2013.01); *B29B 2017/0015* (2013.01); *B29B 2017/0021* (2013.01); *B29B 2017/0203* (2013.01); *B29B 2017/0237* (2013.01); *B29B 2017/0241* (2013.01); *B29B 2017/0265* (2013.01); *B29B 2017/0279* (2013.01); *B29B 2017/0289* (2013.01); *B29B 2017/0296* (2013.01); *B29L 2031/753* (2013.01);
(Continued)

(58) Field of Classification Search
CPC .......................... B09B 3/0075; B02C 18/0084
See application file for complete search history.

(56) References Cited

U.S. PATENT DOCUMENTS

5,116,574 A * 5/1992 Pearson ................... A61L 11/00
                                                          210/173
5,431,347 A * 7/1995 Hayashi ................. B02C 13/282
                                                          241/20
(Continued)

*Primary Examiner* — Jessica Cahill
*Assistant Examiner* — Jared O Brown
(74) *Attorney, Agent, or Firm* — Gregory M. MacDonald, Esq.

(57) ABSTRACT

The present invention comprises a method of shredding treated medical waste, cleaning it of all traces of biological gunk, and sorting it into separate components for recycling. To clean biological gunk from materials, all materials must be first shredded into small parts to expose the interior. The cleaning is performed by submerging the gunk coated materials into a caustic solution that breaks down and dissolves the gunk off of the materials. The caustic solution may comprise sodium hydroxide, potassium hydroxide, or a similar chemical, which is highly effective in producing a corrosive chemical that can break down blood, bone marrow, urine, unused medication, food waste, organs, tissues and any other biologic materials. After all of the biological material is removed from the cleaned materials, they are sorted into component materials, such as plastics, metals, rubbers, glass, etc.

8 Claims, 8 Drawing Sheets

(51) Int. Cl.
  *A61L 11/00* (2006.01)
  *C22B 7/00* (2006.01)
  *B02C 23/14* (2006.01)
  *B02C 23/10* (2006.01)
  *B02C 23/20* (2006.01)
  *B02C 18/00* (2006.01)
  *B29B 17/02* (2006.01)
  *B03C 7/00* (2006.01)
  *B03B 9/06* (2006.01)
  *C22B 1/00* (2006.01)
  *B03C 1/30* (2006.01)
  *B03C 1/035* (2006.01)
  *B29L 31/00* (2006.01)
  *B29B 17/00* (2006.01)

(52) U.S. Cl.
  CPC .............. *Y02P 10/20* (2015.11); *Y02W 30/52* (2015.05); *Y02W 30/62* (2015.05)

(56) References Cited

U.S. PATENT DOCUMENTS

| | | | |
|---|---|---|---|
| 5,656,248 A * | 8/1997 | Kline | A61L 11/00 422/105 |
| 6,113,854 A | 9/2000 | Milum | |
| 6,114,401 A * | 9/2000 | Doonan | B02C 19/0093 521/40 |
| 7,531,080 B2 | 5/2009 | Carson | |
| 8,822,535 B2 | 9/2014 | Roth | |
| 2001/0053869 A1* | 12/2001 | Kaye | A61L 11/00 588/303 |
| 2004/0018112 A1* | 1/2004 | Wilson | B09B 3/0075 422/3 |
| 2005/0126958 A1* | 6/2005 | Bohlig | B03B 9/061 209/19 |
| 2011/0068036 A1* | 3/2011 | Ji | B09B 3/0075 206/524.1 |
| 2015/0258713 A1* | 9/2015 | Valdmaa | B02C 18/18 241/3 |

\* cited by examiner

CLEANING AND SEPARATING MEDICAL WASTE

CROSS-REFERENCE TO RELATED APPLICATION

This application claims the benefit of U.S. Provisional Application Ser. No. 62/425,359, filed 22 Nov. 2016, the entire contents of which is hereby incorporated herein by reference for all purposes as if fully set forth herein, under 35 U.S.C. 119(e).

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR

Not Applicable

BACKGROUND

Unless otherwise indicated herein, the materials described in this section are not prior art to the claims in this application and are not admitted to be prior art by inclusion in this section.

1. Field of the Invention

The present invention relates generally to separating and cleaning treated medical waste into component parts for recycling. More specifically, the present invention is a method of shredding treated medical waste, cleaning it with a caustic solution to remove biological gunk, and sorting the resulting clean materials into separate groups for recycling.

2. Description of Related Art

Medical waste, often referred to as "red bag," is any waste that either comes in contact with hospital care patients, contains bodily fluids, or otherwise contains any potentially infectious materials. These materials may include syringes, scalpels, medicines, operating room waste, sheets, and single-use surgical devices. The following six medical wastes are commonly regulated by states: (1) pathological waste, such as tissues, organs, body parts, and body fluids; (2) human blood and blood products, such as waste blood, serum, plasma and blood products; (3) cultures and stocks of infectious agents, such as microbiological waste, discarded live and attenuated vaccines, and specimens from medical and pathology laboratories, including culture dishes and devices used to transfer, inoculate, and mix; (4) sharps, such as contaminated hypodermic needles, syringes, scalpel blades, Pasteur pipettes, broken glass, and other items that may cause punctures; (5) isolation waste, which is generated by hospitalized patients, who are isolated to protect others from communicable disease; and (6) contaminated animal carcasses, body parts and bedding from animals intentionally exposed to pathogens in research, biologicals production, or in vivo pharmaceuticals testing.

Although there is no universally accepted definition for medical waste, the definitions offered by most regulatory agencies are similar. While some states have adopted the definition found in federal standards, others use either a general definition or define specific wastes and individual categories of waste that are considered infectious. Regardless of the specific definition used, most state and federal agencies differentiate between common medical waste and waste with the potential for causing infection that requires special precautions.

Medical waste with the potential for causing infection is often referred to as regulated medical waste, infectious waste, biomedical waste, etc. Most states require that infectious medical waste be treated before disposal to reduce the risk of contamination to acceptable levels. Most infectious medical waste is treated through incineration, which is the controlled burning of the waste in an incinerator within a permitted medical waste treatment facility. Other methods of treating infectious medical waste include steam sterilization, alternative technologies that treat waste at an extremely high temperature, and other alternative approved treatment methods that result in the destruction of pathogenic microorganisms.

Medical waste is considered noninfectious or "treated" when the process inactivates the following: bacterial spores, cyst forms of parasites, mycobacteria, nonlipid or small viruses, fungi, non-cyst forms of parasites, vegetative bacteria, and lipid or medium-size viruses. Since treated medical waste is still covered with traces of biological gunk such as blood, bile, etc., it is not in a condition where it may be recycled. Thus, in most states, treated medical waste is disposed of in a landfill with general waste. It is estimated that an average hospital will dispose of 50%-70% of their treated medical waste in landfills. This results in approximately 2.4 billion pounds of landfill waste each year in the United States alone. While incineration and heat sterilization are believed to be effective, the potential long-term side effects of burying billions upon billions of pounds of medical waste are currently unknown.

Accordingly, there is a need for a method to recycle treated medical waste that is quick, efficient, and cost-effective, to prevent the waste from being buried in landfills and causing unknown long-term side effects. The method described in this patent application fulfills at least one of these needs or creates other utility.

BRIEF SUMMARY OF THE INVENTION

It is a principal object to solve at least one of the disadvantages with other attempted solutions or to create other utility by providing a method that produces clean materials for component separation and recycling that is quick, efficient, or cost-effective, to prevent it from being buried in landfills and causing unknown long-term side effects.

The present invention relates generally to separating and cleaning treated medical waste into component parts for recycling. More specifically, the present invention is a method of shredding treated medical waste, cleaning it with a caustic solution to remove biological gunk, and sorting the resulting clean materials into separate groups for recycling.

To clean biological gunk from materials, all materials must be first shredded into small parts to expose the interior. The cleaning is performed by submerging the gunk coated materials in a caustic solution that breaks down and dissolves the gunk. The caustic solution may comprise sodium hydroxide, potassium hydroxide, or a similar chemical that is effective in breaking down blood, bone marrow, urine, unused medication, food waste, organs, tissues, or other biologic materials. After all of the biological material is removed from the materials, they are sorted into component materials, such as plastics, metals, rubbers, glass, etc.

The present invention is comprised of a combination of steps and attributes. One step is to create a caustic solution from sodium hydroxide, potassium hydroxide, or a similar chemical. Sodium hydroxide is also known as caustic and lye. When mixed with water, it creates a caustic solution that is highly effective in breaking down blood, bone marrow, urine, unused medication, food waste, organs, tissues, or other biologic materials. A caustic solution is important in cleaning medical waste, because it produces clean materials for component separation and recycling. A caustic solution may also be created by using potassium hydroxide instead of sodium hydroxide. As a result, sodium hydroxide, potassium hydroxide, or another chemical may be used to create a caustic solution that can efficiently eliminate biological material from components, allowing them to be recycled.

BRIEF DESCRIPTION OF THE DRAWINGS

The accompanying drawings, which are incorporated in and constitute a part of this specification, illustrate several aspects described below.

DETAILED DESCRIPTION OF THE INVENTION

It is to be understood that this invention is not limited to any particular embodiment described, which may vary. Also, it is to be understood that the terminology used herein is for the purpose of describing particular embodiments only, and is not intended to be limiting, since the scope of this invention will be limited only by the appended claims.

In the following detailed description, numerous specific details are set forth in order to explain and provide a thorough understanding of the present invention. However, it is apparent that the present invention may be practiced without all of these specific details. Thus, all illustrations of the drawings are for the purpose of describing versions of the present invention, and are not intended to limit the scope of the invention.

In the following section, the present invention is described fully by referencing the details in the enclosed drawings, which illustrate certain embodiments of the invention. The numbers shown in this specification refer to the corresponding numbers in the enclosed drawings. The terminology used is to describe the particular embodiment shown and is not intended to limit the scope of the invention. The invention may also be embodied in many other forms in addition to the embodiments shown. Thus, the embodiments shown should not be construed as limiting, but rather, to allow a thorough and complete description of the disclosure that conveys the scope of the invention to a person having ordinary skill in the art in the field of this invention. Therefore, for the terms used herein, the singular forms "the," "a," and "an" are intended to include the plural forms as well as the singular forms, unless the context clearly indicates otherwise. The term "and" includes any and all combinations of one or more of the associated listed items. As used herein, the terms "comprising" and "comprises" when used in this specification, identify specific steps, integers, operations, features, components, and elements, but do not preclude the presence or addition of one or more other steps, operations, features, components, and elements. In addition, the features, components, and elements referenced may be exaggerated for clarity.

Unless otherwise defined, all scientific terms, technical terms, or other terms used herein have the same meaning as the term that is understood by one having ordinary skill in the art in the field of this invention. It is also understood that these terms, including their dictionary meaning, should be understood as having the meaning, which is consistent with their definitions in the related relevant art. In addition, the present disclosure is not to be interpreted in an idealized or overly formal sense unless expressly stated so herein. Constructions or functions that are well known in the art may not be fully described in detail for brevity.

In describing the invention, it is understood that a number of steps and methods may be disclosed. Each of these may have individual benefit. Also, each may be used in conjunction with at least one or more of the disclosed steps and methods. Therefore, this description will refrain from stating each and every possible combination of the individual steps and methods for the sake of brevity. Regardless, the specification and related claims should be understood with the combinations that are entirely within the scope of the claims and inventions.

The disclosure in this invention are examples of how it may be implemented and are not intended to limit the scope of the invention to the specific embodiments shown in the accompanying drawings or the description provided herein. The present invention will now be described by example in the following paragraphs by referencing the accompanying drawings, which represent embodiments and alternative embodiments.

Figure 1:
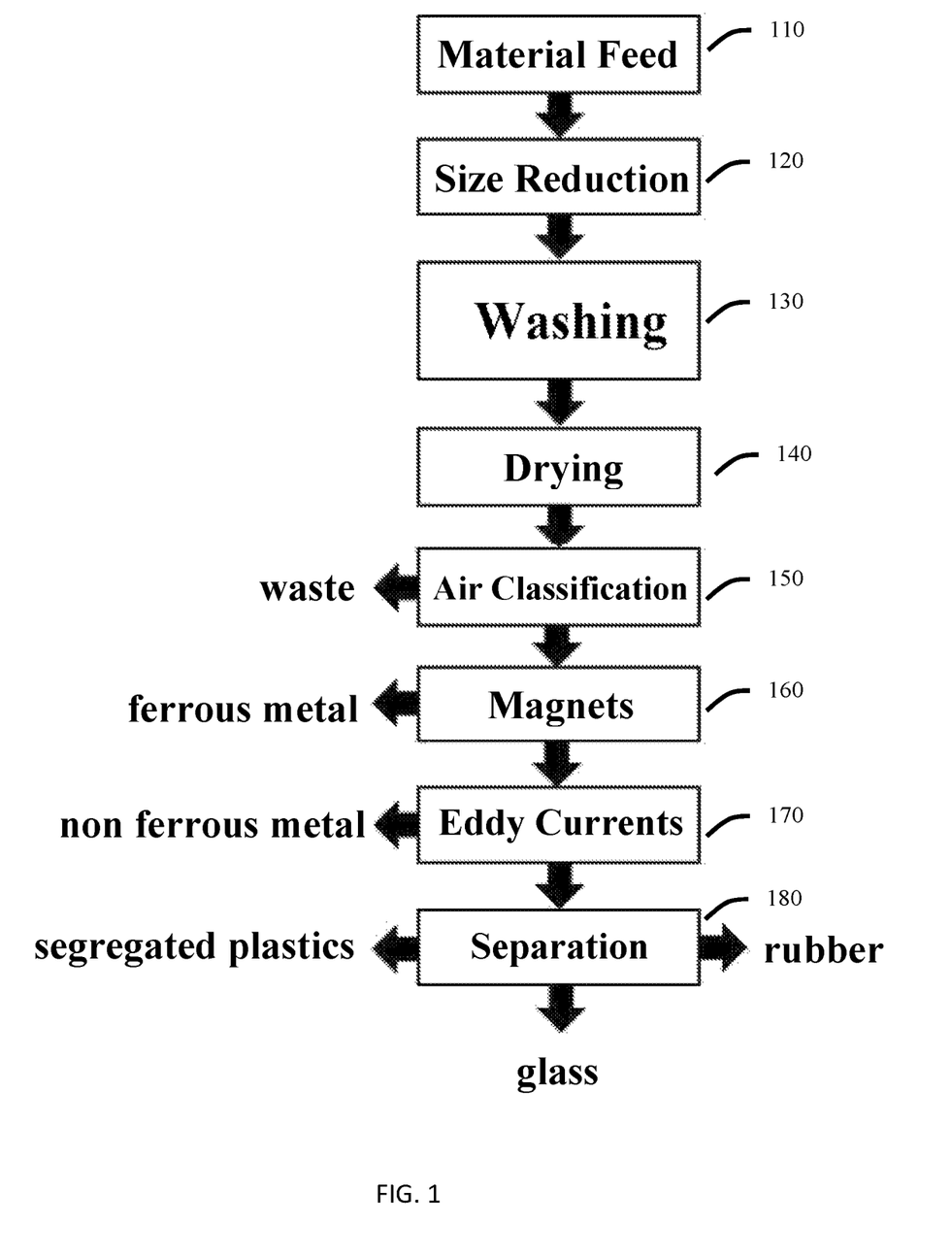
FIG. 1 is a flowchart of a method in which at least one of the embodiments of this invention is implemented.

With reference to FIG. 1, a method of separating and cleaning treated medical waste is described to separate it into its component materials for recycling. The method comprises first receiving treated medical waste, which is known as "Material Feed" 110. Although the Material Feed 110 is noninfectious, it may still be coated with traces of biological gunk, which may include blood, bone marrow, urine, unused medication, food waste, organs, tissues, or other biologic materials.

Next, the Material Feed 110 is reduced in size by shredding it into small parts to expose its interior, in a process known as "Size Reduction" 120. After that, the Material Feed is washed to remove biologic contamination, in a step called "Washing" 130. Specifically, Washing 130 is performed by submerging the gunk coated materials into a caustic solution that may comprise sodium hydroxide, potassium hydroxide, or a similar chemical. This caustic solution is highly effective in producing a corrosive chemical that can break down and dissolve gunk off of the materials. The potential of hydrogen ("pH") level for the caustic solution may preferably be in the range of 11 pH to 12.5 pH, and the temperature of the caustic solution may preferably be in the range of between 120 degrees Fahrenheit ("F") to 140 degrees F.

Next, the materials are dried, in a step called "Drying" 140. After that, the resulting material is separated out using air in a step called "Air Classification" 150. Air Classification 150 is a method of using air pressure to separate light fluffy material, such as gloves, labels, and textiles, from denser materials, such as plastic, glass, and metal.

Next, ferrous metal materials are separated out with magnets, in a step called "Magnets" 160. After that, nonferrous metal materials are separated out with eddy currents in a step called "Eddy Currents" 170. Eddy Currents 170 is a method of extracting nonferrous (nonmagnetic) metals by producing an electromagnetic field that opposes metallic objects. As nonferrous metals pass over the magnetic field, they are pushed out of and ejected from the other materials.

Next, materials are separated based on their density into segregated plastics, rubber, and glass, by Density Separation and/or Near-Infrared Sorting 180. Density Separation is a term used to describe separating materials according to their specific gravity, which is the ratio of the density of a substance to the density of a reference substance. The most common method is to utilize water, which has a specific gravity of approximately 1.0. Its density may be increased by adding salt or decreased by adding isopropyl alcohol. By modifying the density of the liquid, materials with a lower density than the liquid will float while materials with a higher density will sink. By modifying the liquid density, various material separations may be conducted. Similar Density Separation can also be conducted with hydrocyclones, air and other methods. Near-Infrared ("NIR") Sorting, also known as NIR Spectroscopy, involves using the wavelength for different material chemistries of mixed plastics to sort colored resins composed of different polymers. Diffuse reflection measurements are made in the NIR region to capture distinct spectral differences resulting from the unique polymer compositions, while avoiding the detection of spectral differences arising from resin color.

Figure 2:
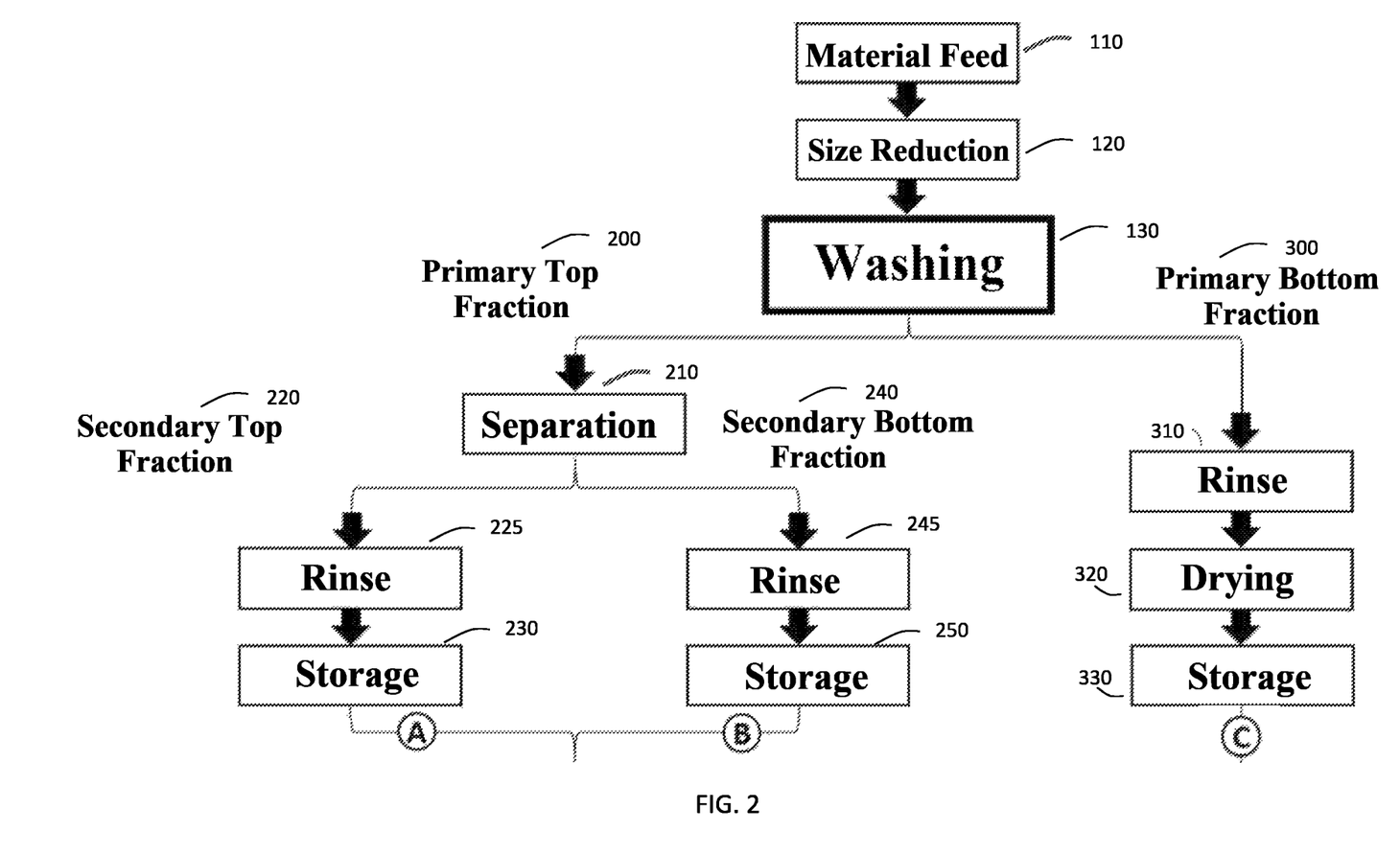
FIG. 2 is a flowchart of the first part of a method in which at least one of the embodiments of this invention is implemented.

FIG. 2 is a flowchart of a method of separating and cleaning treated medical waste to separate it into its component materials for recycling. The method comprises first receiving the Material Feed 110 as described above. Next, Size Reduction 120 reduces the Material Feed 110 in size by shredding it into small parts to expose the interior. The Material Feed 110 then under goes Washing 130 in a sink/float tank with a caustic solution to remove the biologic contamination. The pH level for the caustic solution may preferably be in the range of 11 pH to 12.5 pH, and the temperature of the caustic solution may preferably be in the range of between 120 degrees F. to 140 degrees F.

After that, the washed materials are separated into a Primary Top Fraction group 200 and a Primary Bottom Fraction group 300. The Primary Top Fraction group 200 consists of polypropylene, polyethylene, labels, Styrofoam, fibers, and rubber. Styrofoam is a registered trademark of Dow Chemical Company for a closed-cell extruded polystyrene foam. The Primary Bottom Fraction group 300 consists of glass and metals, such as steel, stainless steel, and titanium.

Next, Density Separation 210 is performed on the Primary Top Fraction group 200 to further separate the materials into a Secondary Top Fraction group 220 and a Secondary Bottom Fraction group 240. The Secondary Top Fraction group 220 consists of polypropylene, polyethylene (high density and low density), labels, and Styrofoam. The Secondary Bottom Fraction group 240 consists of fibers, rubber, heavy plastics, gloves, nylon, Acrylonitrile Butadiene Styrene ("ABS"), textiles, and trash.

The Secondary Top Fraction 220 materials are then rinsed, in a step called Rinse 225, and then stored in a feeder bin 230. Similarly, the Secondary Bottom Fraction 240 materials are rinsed, in a step called Rinse 245, and stored in a feeder bin 250. The Primary Bottom Fraction materials 300 are also rinsed (Rinse 310), dried (Drying 320), and placed in feeder bins 330 for storage.

Figure 3:
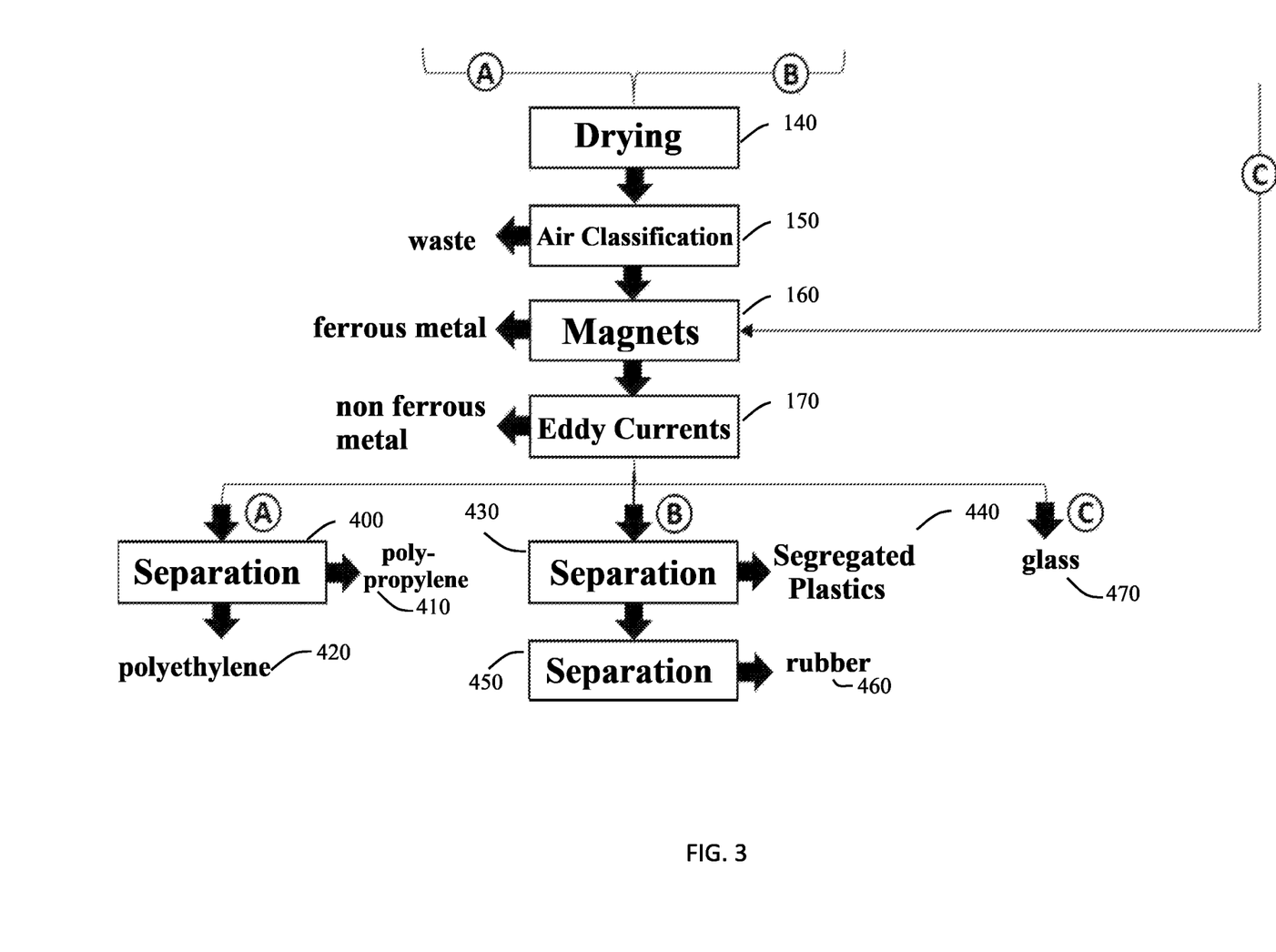
FIG. 3 is a flowchart of the second part of a method in which at least one of the embodiments of this invention is implemented.

Next, as shown in FIG. 3, the Secondary Top Fraction 220 and the Secondary Bottom Fraction 240 groups are dried (Drying 140). After that, these materials are separated with Air Classification 150 to separate out the light fluffy waste materials, such as labels, low density polyethylene, Styrofoam, gloves, fibers, and textiles, which leaves the denser materials, such as heavier plastics, glass, and metal. Next, ferrous metal waste are separated out from these materials using Magnets 160. After that, nonferrous metal waste in these materials are separated out with Eddy Currents 170. Similarly, as shown in FIG. 3, the ferrous metal waste in the Primary Bottom Fraction materials 300 materials are separated out with Magnets 160, and the nonferrous metal waste are separated out with Eddy Currents 170.

The next step involves using density and/or electrostatic separation 400 to separate the materials into separate groups of polypropylene 410 or high density polyethylene 420. Also, segregated plastics, such as polypropylene, polyethylene, nylon, ABS and other heavy plastics are separated with Density Separation 430. Density Separation 450 is also used to separate out rubber 460. In addition, glass 470 is separated out.

Figure 4:
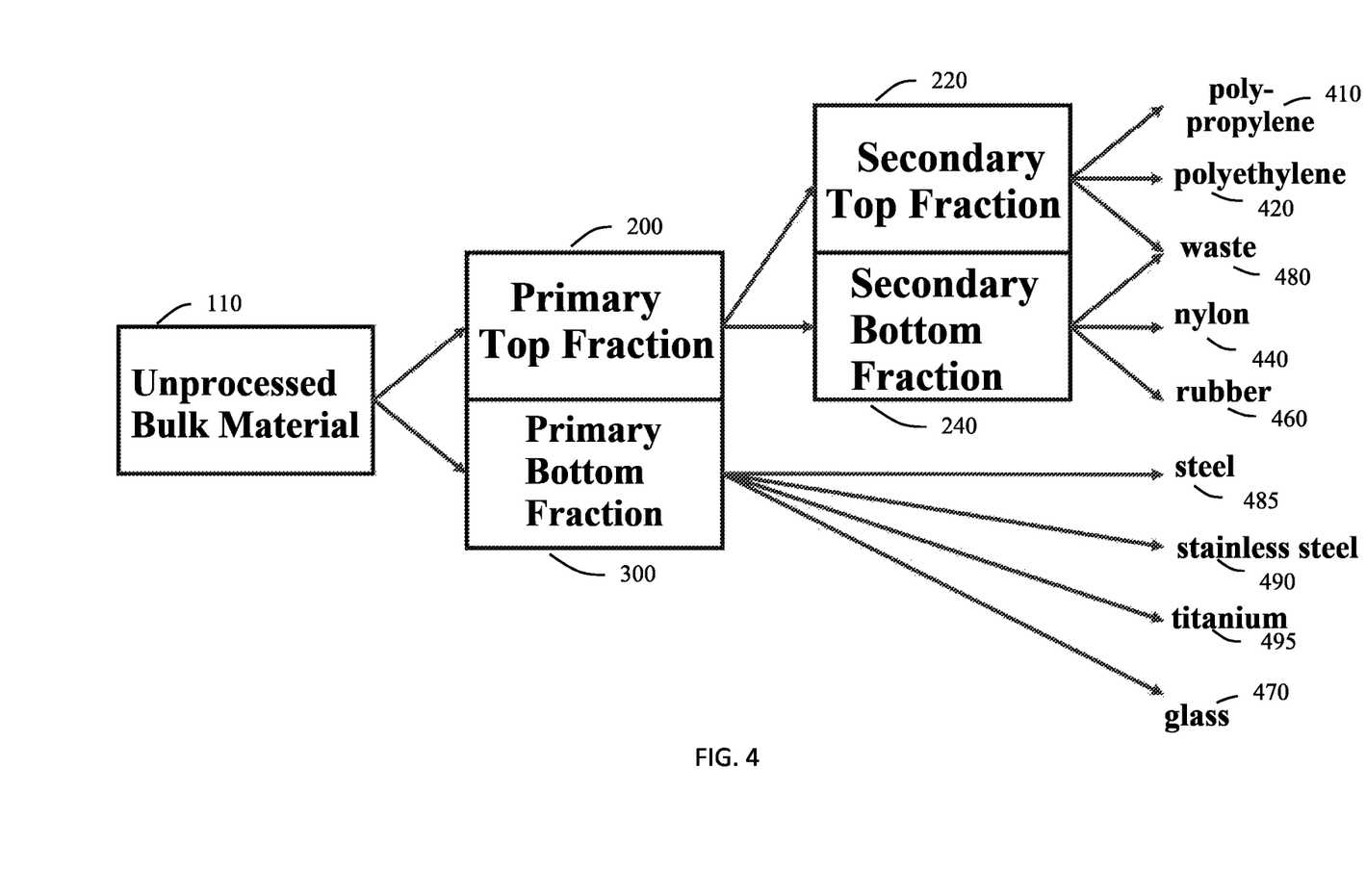
FIG. 4 is a fraction diagram of a method in which at least one of the embodiments of this invention is implemented.

With reference to FIG. 4, further details are explained regarding the various stages of separation. The first stage involves separating the unprocessed bulk material, known as Material Feed 110. During the first stage, the Material Feed 110 is separated into a Primary Top Fraction group 200, which comprises polypropylene, polyethylene, rubber, gloves, nylon, ABS, other plastics, textiles, and trash; and a Primary Bottom Fraction group 300, which comprises glass and metal.

The Primary Top Fraction group 200 is further separated into a Secondary Top Fraction group 220, which comprises polypropylene, polyethylene, PE labels, some gloves, and textiles, and a Secondary Bottom Fraction group 240 or "Middle Fraction," which is comprised of rubber, gloves, nylons, ABS, other plastics, textiles, and trash.

Next, the Secondary Top Fraction group 220 is divided into polypropylene 410; polyethylene (regrind) 420; and PE labels, gloves, textiles, and waste 480. The Secondary Bottom Fraction group 240 is divided into PE labels, gloves, textiles, and waste 480; nylon, ABS, and other plastics 440;

and rubber 460. Finally, the Primary Bottom Fraction group 300 is separated into steel 485, stainless steel 490, titanium 495, and glass 470.

Figure 5:
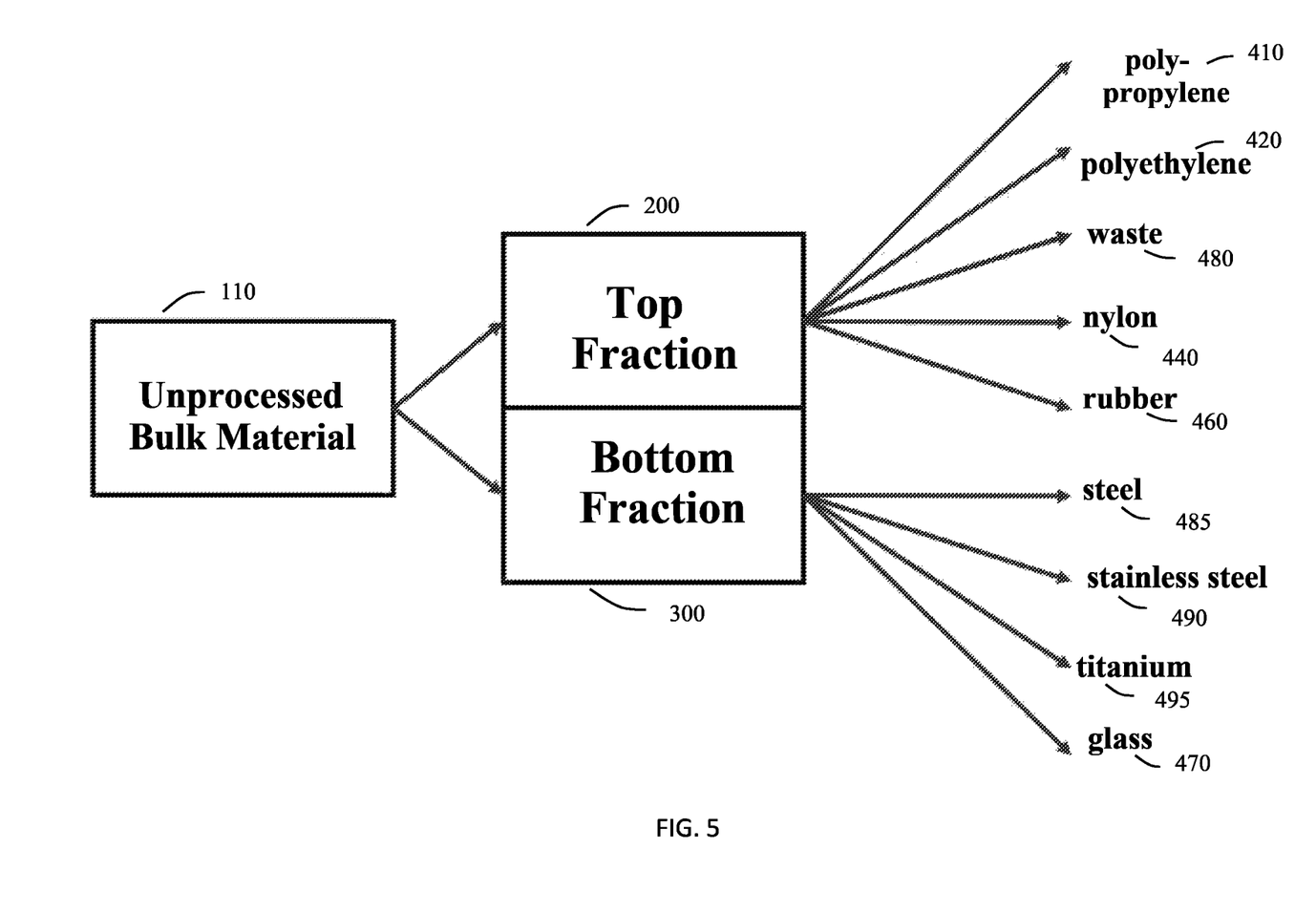
FIG. 5 is an alternative embodiment of a fraction diagram of a method in which at least one of the embodiments of this invention is implemented.

In at least one alternative embodiment, as shown in FIG. 5, an optional method with less steps is shown for reducing the number of stages of separation. The first stage still involves separating the Material Feed 110 into a Primary Top Fraction group 200 and a Primary Bottom Fraction group 300. The Primary Top Fraction group 200 is then directly separated into polypropylene 410; polyethylene 420; labels, gloves, textiles, and waste 480; nylon, ABS, and other plastics 440; and rubber 460. The Primary Bottom Fraction group 300 is still directly separated into steel 485, stainless steel 490, titanium 495, and glass 470.

Figure 6:
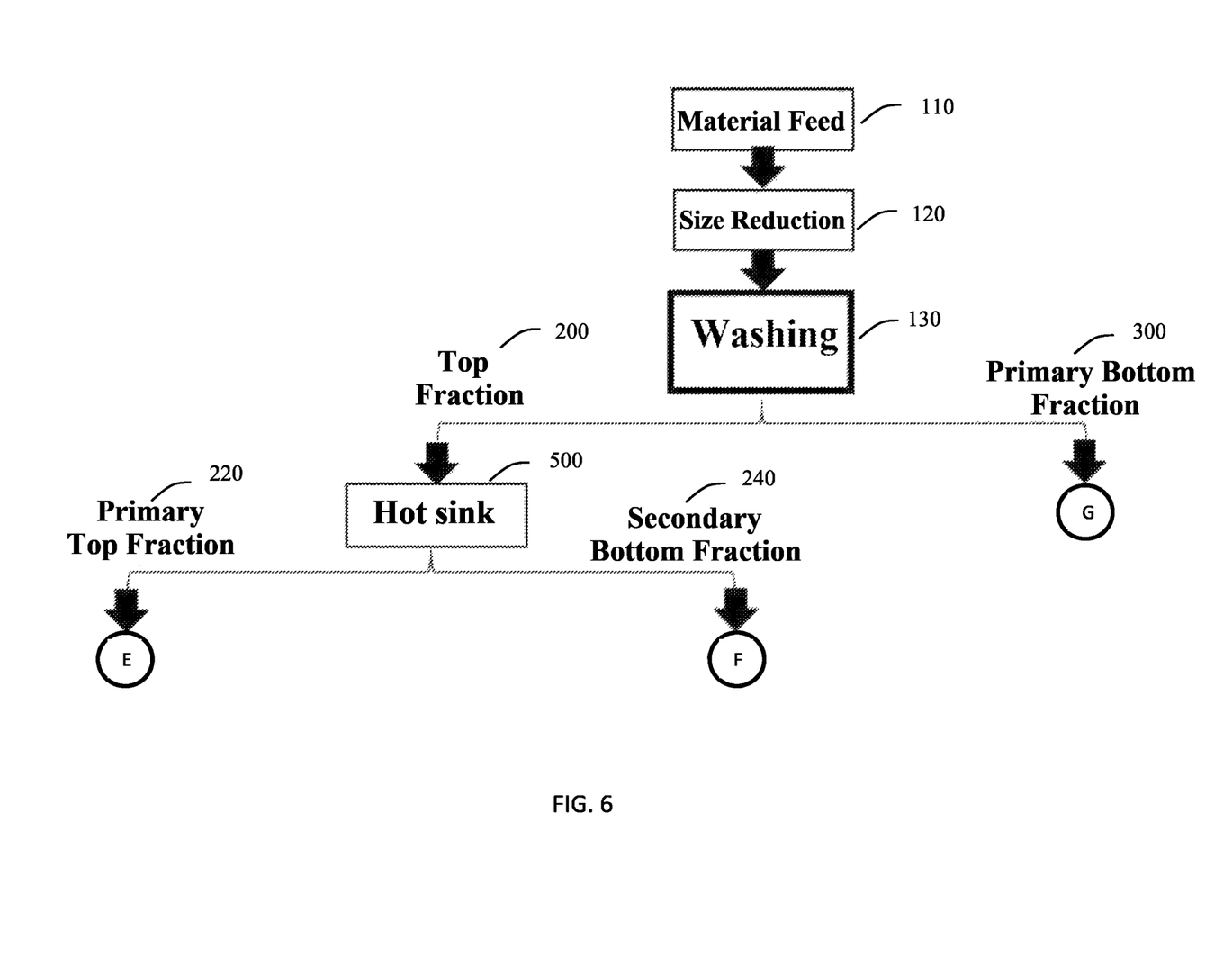
FIG. 6 is an alternative embodiment of a flowchart of the first part of a method in which at least one of the embodiments of this invention is implemented.

With reference to FIG. 6, an alternative method of separating and cleaning treated medical waste is described to separate it into its component materials for recycling. The method comprises first receiving Material Feed 110. Next, the Material Feed 110 under goes Size Reduction 120 by shredding it into small parts to expose the interior. The Material Feed 110 is then washed in a caustic solution in a hot sink/float tank to remove the biologic contamination in a step called Washing 130. Washing 130 is performed by submerging the gunk coated materials into a caustic solution that may comprise sodium hydroxide, potassium hydroxide, or a similar chemical. This caustic solution Washing 130 is highly effective in producing a corrosive chemical that can break down and dissolve gunk off of the materials. The pH level for the caustic solution may preferably be in the range of 11 pH to 12.5 pH, and the temperature of the caustic solution may preferably be in the range of between 120 degrees F. to 140 degrees F.

Next, the washed materials are separated into a Top Fraction group 200 that comprises polypropylene, polyethylene, labels, Styrofoam, fibers, and rubbers; and a Primary Bottom Fraction group 300 that comprises glass and metals, such as steel, stainless steel, and titanium. After that, a hot sink/float tank 500 is used to separate the Top Fraction group 200 into a Primary Top Fraction group 220 which comprises polypropylene, polyethylene (high density and low density), labels, and Styrofoam; and a Secondary Bottom Fraction group 240, which comprises fibers, rubber, heavy plastics, gloves, nylon, ABS, textiles, and trash.

Figure 7:
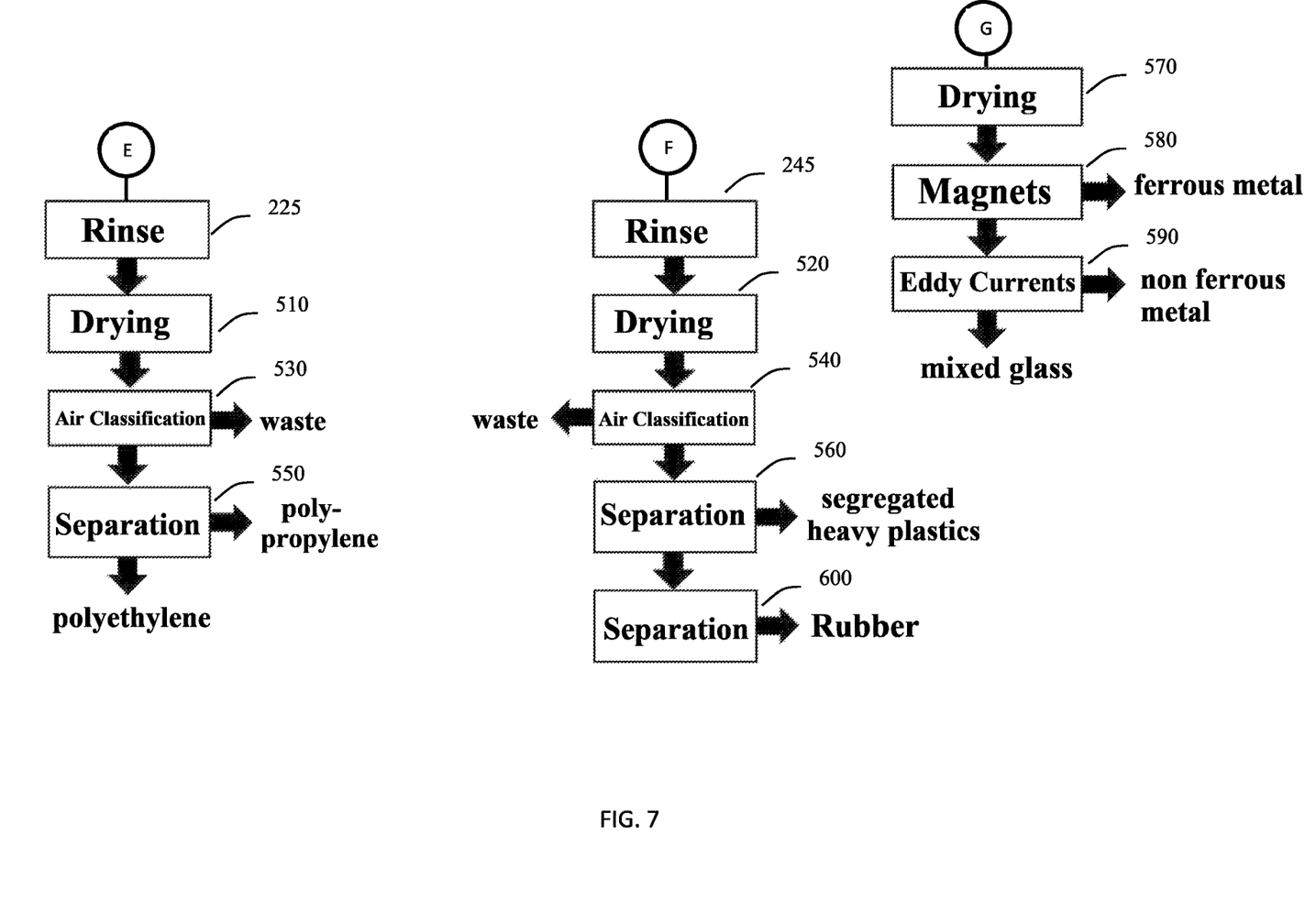
FIG. 7 is an alternative embodiment of a flowchart of the second part of a method in which at least one of the embodiments of this invention is implemented.

FIG. 6 at point "E" continues to point "E" on FIG. 7 to a step entitled Rinse 225, which involves rinsing the Primary Top Fraction 220 materials. Next, the materials are dried in a step entitled Drying 510. After that, the materials are separated in a step called Air Classification 530, which separates out waste such as, labels, low density polyethylene, Styrofoam, gloves, fibers, and textiles. After that, Density Separation and/or Electrostatic Separation 550 is used to separate the materials into polypropylene and high density polyethylene.

FIG. 6 at point "F" continues to point "F" on FIG. 7, where a step entitled Rinse 245 involves rinsing the Secondary Bottom Fraction group 240 materials. After that, in a step entitled Drying 520, the materials are dried. Next, the materials are separated in a step called Air Classification 540, which separates out waste such as, labels, low density polyethylene, Styrofoam, gloves, fibers, and textiles. After that, Density Separation 560 is used to separate the materials into segregated heavy plastics, such as nylon, ABS, and other heavy plastics. Density Separation 600 is used to separate out rubber.

FIG. 6 at point "G" continues to point "G" on FIG. 7, where a step entitled Drying 570, involves drying the Primary Bottom Fraction 300 materials. After that, Magnets 580 are used to separate out the ferrous metal materials. Next, nonferrous metal materials and mixed glass cullet are separated out with Eddy Currents 590, which extracts nonferrous metals by producing an electromagnetic field.

Figure 8:
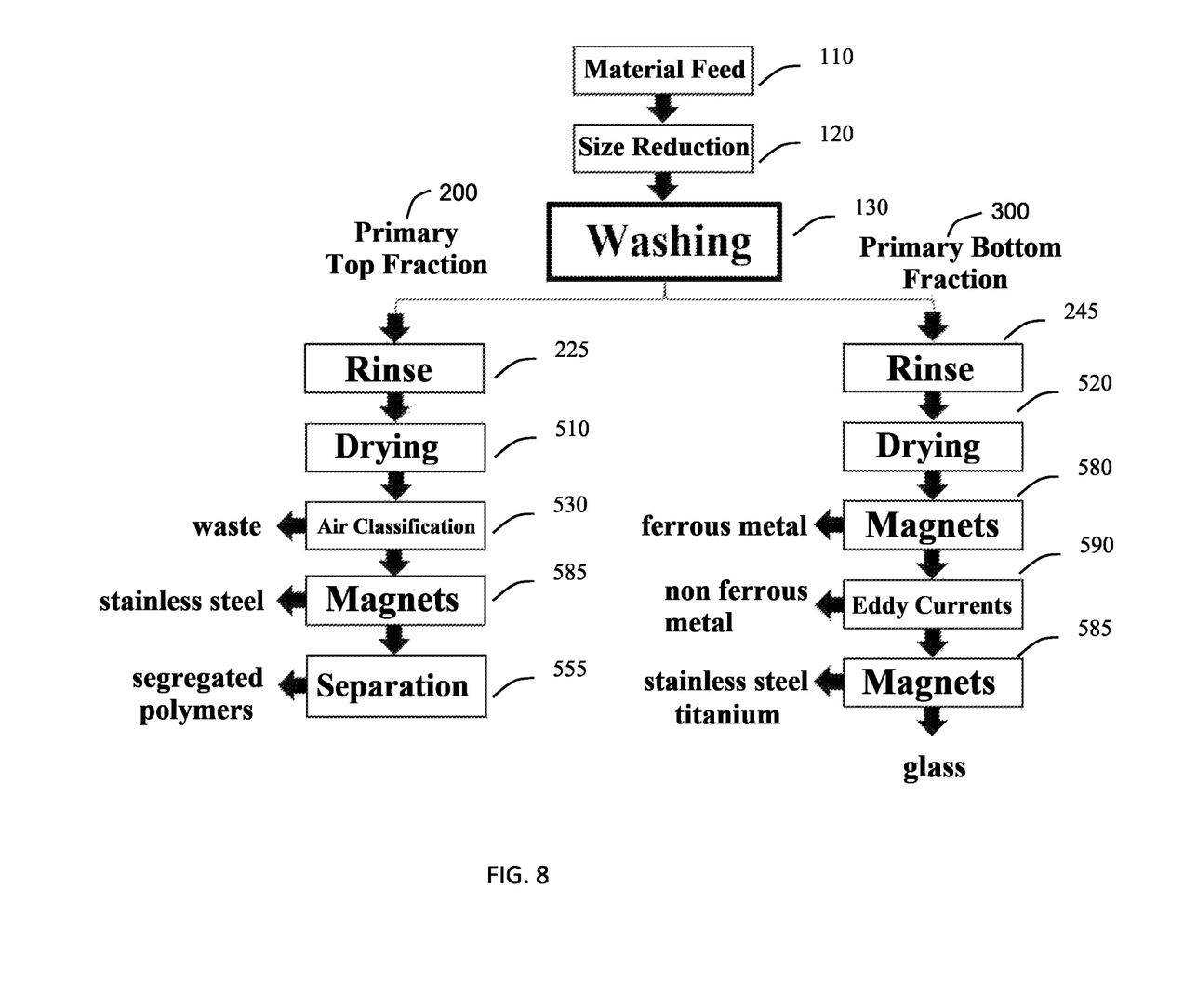
FIG. 8 is another alternative embodiment of a flowchart of a method in which at least one of the embodiments of this invention is implemented.

With reference to FIG. 8, another alternative method of separating and cleaning treated medical waste is described to separate it into its component materials for recycling. The method comprising first receiving Material Feed 110. Next, the Material Feed 110 undergoes Size Reduction 120 by shredding it into small parts to expose the interior. The Material Feed 110 is then washed in a caustic solution in a hot sink/float tank to remove biologic contamination during Washing 130, where the gunk coated materials are submerged into a caustic solution that may comprise sodium hydroxide, potassium hydroxide, or a similar chemical. This caustic solution Washing 130 is highly effective in breaking down and dissolving gunk off of the materials. The pH level for the caustic solution may preferably be in the range of 11 pH to 12.5 pH, and the temperature of the caustic solution may preferably be in the range of between 120 degrees F. to 140 degrees F.

The materials are then separated into a Primary Top Fraction group 200 that comprises polypropylene, polyethylene, labels, Styrofoam, fibers, and rubbers; and a Primary Bottom Fraction group 300 that comprises glass and metals, such as steel, stainless steel, and titanium.

Next, the Primary Top Fraction group 200 further undergoes Rinse 225, where the materials are rinsed. After that, the materials undergo a step called Drying 510, where the materials are dried. Next, the materials are separated in a step called Air Classification 530. After that, high intensity Magnets 585 are used to separate out stainless steel. Next, Density Separation and/or NIR Sorting 555 is used to separate the materials into polypropylene, polyethylene, polystyrene, nylon, ABS, Polyethylene Terephthalate ("PET"), rubber, and other heavy plastics. As previously discussed, NIR Sorting involves using the wavelength for different material chemistries of mixed plastics to sort colored resins composed of different polymers.

The materials in the Primary Bottom Fraction group 300 are also rinsed in a step entitled Rinse 245. After that, in a step entitled Drying 520, the materials are dried. Next, the ferrous metal materials are separated out with Magnets 580. After that, the nonferrous metal materials are separated out with Eddy Currents 590. Next, High Intensity Magnets 585 separate the materials into stainless steel, titanium, and glass.

All of these embodiments and the invention disclosed herein are intended to be within the scope herein disclosed. These and other embodiments of the invention will become readily apparent to those skilled in the art from the detailed description of the preferred embodiments having reference to the attached figures, the embodiments not being limited to any particular, preferred embodiments disclosed. Also, the invention disclosed herein suitably may be practiced in the absence of any element which is not specifically disclosed herein.

What is claimed is:
1. A method of cleaning and separating treated medical waste into component materials for recycling, the method comprising:
   first receiving material feed;
   second reducing the size of the material feed;
   third washing the material with a caustic solution comprising of potassium hydroxide to remove biologic contamination, wherein the caustic solution has a pH of about 11 pH to 12.5 pH and a temperature of about 120 degrees F. to 140 degrees F.;

fourth separating the washed material into a primary top fraction group comprising polypropylene, polyethylene, labels, polystyrene, fibers, rubbers, gloves, nylon, acrylonitrile butadiene styrene (ABS), and textiles; a primary bottom fraction group comprising glass and metals;

fifth performing a density separation to separate the primary top fraction group into a secondary top fraction group comprising polypropylene, polyethylene, labels, and polystyrene, and a secondary bottom fraction group comprising fibers, rubber, plastics selected from the group consisting of nylon, ABS, and gloves, and textiles;

sixth rinsing the materials in the secondary top fraction group, the secondary bottom fraction group, and the primary bottom fraction group;

seventh drying the materials in the primary bottom fraction group;

eight storing the materials in the secondary top fraction group, the secondary bottom fraction group, and the primary bottom fraction group in feeder bins;

ninth drying the materials in the secondary top fraction group and the secondary bottom fraction group;

tenth separating the materials in the secondary top fraction group and the secondary bottom fraction group with air classification;

eleventh separating out ferrous metal material from the secondary top fraction group, the secondary bottom fraction group, and the primary bottom fraction group using magnets;

twelfth separating out nonferrous metal material from the secondary top fraction group, the secondary bottom fraction group, and the primary bottom fraction group using eddy currents; and thirteenth separating out the remaining materials in the secondary top fraction, secondary bottom fraction, and primary bottom fraction groups into polypropylene, polyethylene, rubber, glass, nylon, and ABS.

2. The method of claim 1, wherein the remaining materials are separated out using near-infrared sorting.

3. The method of claim 1, wherein the remaining materials are separated out using density separation.

4. A method of cleaning and separating treated medical waste into component materials for recycling, the method comprising:

first receiving material feed;

second reducing the size of the material feed;

third washing the material with a caustic solution comprising of potassium hydroxide to remove biologic contamination, wherein the caustic solution has a pH of about 11 pH to 12.5 pH and a temperature of about 120 degrees F. to 140 degrees F.;

fourth separating the washed material into a top fraction group comprising polypropylene, polyethylene, labels, polystyrene, fibers, rubbers, gloves, nylon, ABS, and textiles;

fifth separating the washed material into a primary bottom fraction group comprising glass and metals;

sixth drying the materials in the primary bottom fraction group;

seventh separating out ferrous metal material from the primary bottom fraction group using magnets;

eight separating out nonferrous metal material from the primary bottom fraction group using eddy currents ninth using a hot sink float tank to separate the top fraction group into a primary top fraction group comprising polypropylene, polyethylene, labels, and polystyrene, and a secondary bottom fraction group comprising fibers, rubber, plastics, gloves, nylon, ABS, and textiles;

tenth rinsing the materials in the primary top fraction group and the secondary bottom fraction group;

eleventh drying the materials in the primary top fraction group and the secondary bottom fraction group;

twelfth using air classification to separate waste from the materials in the primary top fraction group and the secondary bottom fraction group;

thirteenth separating the remaining materials in the primary top fraction group into polypropylene and high density polyethylene; and fourteenth using density separation to separate the materials in the secondary bottom fraction group into plastics, nylon, ABS, and rubber.

5. The method of claim 4, wherein the remaining materials are separated out using density separation.

6. A method of cleaning and separating treated medical waste into component materials for recycling, the method comprising:

first receiving material feed;

second reducing the size of the material feed;

third washing the material with a caustic solution comprising of potassium hydroxide to remove biologic contamination wherein the caustic solution has a pH of about 11 pH to 12.5 pH and a temperature of about 120 degrees F. to 140 degrees F.;

fourth separating the washed material into a primary top fraction group comprising polypropylene, polyethylene, plastics, labels, polystyrene, fibers, rubber, gloves, nylon, ABS, and textiles;

fifth separating the washed material into a primary bottom fraction group comprising glass and metals;

sixth rinsing the materials in the primary top fraction group and the primary bottom fraction group;

seventh drying the materials in the primary top fraction group and the primary bottom fraction group;

eight separating the materials in the primary top fraction group with air classification;

ninth separating the materials in the primary top fraction group with magnets;

tenth separating the remaining materials in the primary top fraction group into polypropylene, polyethylene, polystyrene, plastics, nylon, ABS, and rubber;

eleventh separating the materials in the primary bottom fraction group with additional magnets; and twelfth separating out nonferrous metal material from the primary bottom fraction group using eddy currents.

7. The method of claim 6, wherein the remaining materials are separated out using near infrared sorting.

8. The method of claim 6, wherein the remaining materials are separated out using density separation.

\* \* \* \* \*